United States Patent [19]

Seno et al.

[11] Patent Number: 4,722,917

[45] Date of Patent: Feb. 2, 1988

[54] ANTI-I SORBENT

[75] Inventors: Taiko Seno, Osaka; Yasuto Okubo, Nara; Masao Kawamura, Akashi; Seiichi Akutsu, Kakogawa; Hirosuke Fukuda, Himeji, all of Japan

[73] Assignee: Seitetsu Kagaku Co., Ltd., Hyogo, Japan

[21] Appl. No.: 699,571

[22] Filed: Feb. 7, 1985

[30] Foreign Application Priority Data

Feb. 7, 1984 [JP] Japan ................................ 59-21491

[51] Int. Cl.[4] ..................... B01J 37/36; B01J 20/24; B01J 20/16; B01J 20/26
[52] U.S. Cl. .................................... 502/7; 210/690; 435/7; 436/825; 502/62; 502/402; 502/403; 502/404; 514/8; 514/54
[58] Field of Search ................ 502/7, 62, 401–404; 210/927, 679, 690; 436/825, 824, 547, 532, 515, 513, 175, 178; 435/7; 514/8, 54

[56] References Cited

U.S. PATENT DOCUMENTS 3,442,819  5/1969  Herbert ............................ 502/403
4,379,839  4/1983  Spiegelman ..................... 436/172

OTHER PUBLICATIONS

The Journal of Clinical Investigation–vol. 50–1971–pp. 864, 867.
Biological Corporation of America, "RESt, For Removal of Unwanted Cold Agglutinins (Such as Anti I, –H, or –IH) as an Aid in Antibody Detection and Identification", May 1982, 3 pages.
S. T. Liu & Co., "Rabbit Erythrocyte Stroma (RESt) of Biological Corporation of America", 1984, 8 pages.

*Primary Examiner*—Paul E. Konopka
*Attorney, Agent, or Firm*—Pollock, Vande Sande & Priddy

[57] ABSTRACT

An anti-I sorbent which comprises as I blood group substances at least two materials selected from the group consisting of mucin and milk derived from Eutheria and ovomucoid from Ornithurae. The use of the anti-I sorbent inhibits the formation of false positive agglutination caused by anti-I autoantibody.

16 Claims, No Drawings

ANTI-I SORBENT

This invention relates to a sorbent for anti-I. More particularly, the object of this invention is to provide a simple and inexpensive anti-I sorbent for preventing confusing reactions by specifically absorbing anti-I which often causes false positive reactions in blood examinations such as the cross matching test, antibody screening and the like at blood transfusion, and thereby carrying out these examinations exactly and rapidly.

It is well known that the presence of so-called cold agglutinins, in particular, cold autoantibody affects blood group typing, antibody screening, cross matching test and the like to become a serious obstacle to blood transfusion test. Among the cold agglutinins, the presence of anti-I autoantibody is particularly troublesome. The anti-I autoantibody is an antibody possessed by almost everybody and has a nature of agglutinating red blood cells of the person himself or another person at low temperatures. Its titer is very low for a normal human, but in the case of certain diseases or infections such as Mycoplasma pneumonia, autoimmune hemolytic anemia and the like, the titer is increased and the range of reaction temperature is enlarged, so that the anti-I autoantibody often becomes an obstacle to the examinations. The simplest mistake is to interpret a blood specimen to be of AB type in ABO blood grouping. Although such a primitive mistake is an extreme example, there is also the following obstacle. In the case of a specimen in which a cold autoantibody is present, the antibody reacts with an antigen on red blood cells in vivo or in vitro, whereby a complement is bound to the red blood cells. Even when the red blood cells in such a state is washed with a warm saline, the complement still remains on the red blood cells, though the antibody is washed off. In the case of such red blood cells, when the reaction is conducted by using an antibody which can be detected only by Coomb's test, for example, anti $Fy^a$, accurate results can be obtained where Coomb's reagents used are anti IgG, but in some cases, a false positive reaction occurs when polyspecific anti-IgG reagents are used. Interference based on complement-fixing of cold antibodies which can take place in said Coomb's test should also be given attention as an example of obstacle by anti-I's.

As a method for preventing obstacles to the examinations by cold autoantibodies, in particular, by anti-I autoantibody, it is considered to carry out the examinations after previously adsorbing, absorbing or removing anti-I present in a test serum. For this purpose, the absorption and removal of anti-I by patient's own red blood cells has heretofore often been conducted, but this method is disadvantageous, for example, in that its procedure is troublesome and that the absorption is not always complete. On the other hand, a saline suspension of rabbit erythrocyte stroma is used as a reagent for absorbing and removing such anti-I, but it has been disadvantageous in viewpoint of specificity to anti-I and cost.

In order to solve the problems of the prior art in removing the influence of anti-I in the blood transfusion test as described above, the present inventors have devoted themselves to research on a reagent which makes it possible to adsorb, or absorb and remove anti-I easily and inexpensively, and consequently, have found, as substances having a I blood group activity, mucin derived from class IX Mammalia, subclass IX-3 Theria, infraclass 3 Eutheria, order 26 Antiodactyla, suborder 1 Suiformes, 3 Eutheria order 26 Antiodactyla, suborder 3 Ruminantia, 3 Eutheria order 25 Perissodactyla, 3 Eutheria order 25 Perissodactyla suborder 1 Equoidea, and 3 Eutheria order 9 Cagomorpha; milk of a human or 3 Eutheria order 26 suborder 3 Ruminantia; and ovomucoid derived from class VIII Aves, subclass VIII-3 Ornithurae, order 16 Galli, suborder 1 Galli, and have found that anti-I can very markedly be neutralized by acting on them as a mixture thereof, whereby this invention has been accomplished.

That is to say, the gist of this invention is an anti-I absorbing reagent comprising at least two substances selected from the group consisting of mucin and milk derived from Eutheria and ovomucoid derived from Ornithurae. This invention is characterized by binding these substances to an insoluble carrier to support the same thereon.

The anti-I autoantibody which is the subject for this invention is explained below in more detail. Anti-I's are classified into 4 groups (anti-$I^F$, anti-$I^D$, anti-$I^T$ and anti-$I^S$) according to difference in agglutination with OI type red blood cells, O type cord cells and Oi type red blood cells. Most of anti-I's are anti-$I^F$ or anti-$I^D$. The superscripts F and D designate the main constituents of I antigen with which the individual antibodies react. The superscript F stands for "fetal" and is considered to be an I fraction common to all human red blood cells including i type red blood cells of an adult, cord cells and the like. Monkey's red blood cells also possess this antigen. The superscript D of $I^D$ is a symbol derived from the word "developed", and cord cells, i type red blood cells and monkey's red blood cells lack this antigen. Anti-$I^T$ is an antibody found in 1966 and reacts, unlike conventional anti-I's, most strongly with cord cells. Accordingly, the name "$I^T$" is given to an antigen which appears in cord cells at the time of a transition from i to I. The superscript T is derived from the word "transient". On the other hand, anti-$I^S$ is a very rare antibody, and is repressed only by saliva and hence called so after saliva.

The I blood group substances used in this invention include mucin derived from Eutheria, particularly from Suiformes, Ruminantia, Equoidea or Lagomorpha; human milk and milk of Eutheria, particularly of Ruminantia, ovomucoid derived from Ornithurae particularly from Galli; and the like, and the main constituents of these substances are saccharides and/or glycoproteins.

To Suiformes belong Sus, Phacochoesus, Babirussa, Hippopotamus, etc. To Ruminantia belong Cervus, Rangifer, Giraffa, Bubalus, Bos, Poëphagus, Cupra, Ovis, etc. To Equoidea belong horse (Equus), ass, zebra, etc. To Lagomorpha belong Ochotona, Lepus, Pentalagus, Oryctolagus, etc. To Galli belong Lagopus, Coturnix, Bambusicola, Syrmaticus, Argusianus, Paro, Gallus, Meleagris, etc. Although all these animals can be used as sources of the I blood group substances of this invention, an explanation is given below, taking the case of Sus (hog) for Suiformes, bovine and sheep for Ruminantia, horse for Equoidea, Oryctolagus (rabbit) for Lagomorpha, and Gallus (hen) for Galli.

The present inventors have found that there can be used, as a constituent of the sorbent of this invention, mucin derived from hog which is obtained by separation and purification from hog submaxillary gland, gastric mucosa or the like according to a well-known method, and mucin derived from hog stomach which is commerically available as a reagent. It has also been found that both of these mucins give a good result in absorption of, in particular, anti-$I^F$ among anti-I autoantibodies. Next, it has been found that all of mucins derived from bovine, sheep and horse which are obtained by separation and purification from their submaxillary gland, gastric mucosa or the like according to a well-known method give a good result in adsorption of anti-$I^F$ and anti-$I^D$ and can be used as a constituent of the sorbent of this invention. Further, it has been found that rabbit's mucin obtained by separation and purification from rabbit gastric mucosa, intestinal mucosa or the like according to a well-known method markedly absorbs not only anti-$I^F$ but also anti-$I^D$ and can be used as a constituent of the sorbent of this invention. In addition, it has been found that although as the human milk and cow's milk, those obtained by milking are used as they are, I blood group substances derived from these milks satisfactorily absorb anti-$I^T$ and anti-$I^S$. It has also been found that when there is used whey obtained by skimming these milks by centrifugation or the like and then removing casein by acid treatment, a clearer judgement can be passed, so that favorable results can be obtained. However, commercially available processed milk is not preferable because in some cases, it does not absorb anti-$I^T$ and anti-$I^S$. It has also been found that both egg white ovomucoid obtained by separation and purification from hen's egg white according to a well-known method and ovomucoid which is on the market as a reagent are markedly effective for absorbing anti-$I^D$. In addition, it has been found that when a glycopeptide obtained by hydrolyzing ovomucoid with a protease such as pronase is used, a clearer judgement can be passed, so that more favorable results can be obtained.

However, since it is impossible to know previously what kind of antibody among anti-I's is contained in a test serum, it is necessary to use the above-mentioned blood group substances as a mixture thereof. In some cases, two or more kinds of anti-I's are contained in a test serum, and hence the above-mentioned specific blood group substances do not always show the same repression pattern. The finding that in practice, a mixture of at least two kinds of these blood group substances should therefore be used is also a patentable point and an excellent effect of this invention.

As a method for adsorbing or absorbing anti-I's by using these I blood group substances, it is sufficient to merely add 0.05 to 10 mg each of at least two of the above-mentioned blood group substances per ml of serum, but of course, the addition thereof of more than said amount is possible, to a test serum before the examinations. As a method for the addition, there may be conducted either direct addition of the blood group substances or addition of a solution prepared by dissolving the blood group substances in a suitable solvent such as saline or the like. Further, these blood group substances can also be used found to water-insoluble carrier particles, and in some cases, such a way of using is more convenient.

The absorption of anti-I's by the I blood group substances is conducted at 15° to 40° C., preferably at 22° to 37° C. for 5 to 30 minutes, preferably for 10 to 20 minutes. After completion of the reaction, it is sufficient to carry out the examinations without any treatment (in the case of using soluble blood group substances) or after separating insoluble carrier particles by a suitable means such as filtration, centrifugation or the like (in the case of using blood group substances bound to the carrier particles).

As described above, the I blood group substances may be used either in a free form or in a form supported on insoluble carrier particles. As the carrier particles used in this invention, latices of organic high polymers obtained by emulsion polymerization such as polystyrene and styrene-butadiene copolymer, or inorganic oxides such as silica, alumina and zeolite give favorable results.

In this invention, for supporting the I blood group substances on such insoluble carrier particles (i.e., sensitising of said substances), the blood group substances may be adsorbed on the carrier either physically or chemically. In general, the sensitisation is conducted by bringing the I blood group substances dissolved in a concentration of 0.001 to 1% into contact with zeolite particles dispersed in a concentration of 0.01 to 1% in a buffer solution having a pH of 4 to 10 with gentle sitrring at 4° to 60° C. for about 15 minutes to 2 hours. As the buffer solution, there may be used, for example, an acetate buffer solution, a phosphate buffer solution or a glycine buffer solution. After completion of the sensitisation, the carrier particles are washed several times with a buffer solution having a pH around neutrality such as a phosphate buffer or the like, finally suspended in a suspension, and then stored. As the suspension, there is used a suspension prepared by adding 0.01 to 0.5% of sodium azide ($NaN_3$) to a phosphate buffer or the like.

Hereunder, some embodiments of this invention are explained in more detail with reference to Examples.

EXAMPLE 1

Distilled water was added to 216 g of hog gastric mucosa, and the resulting mixture was homogenized by means of a mixer. After the pH of the supernatant obtained by centrifugation was adjusted to 2 with hydrochloric acid, pepsin was added thereto and digestion was conducted at 37° C. for 4 days. A supernatant was obtained by centrifugation, followed by adding thereto ethanol 2.5 times volume as much as the supernatant. The precipitate thus obtained was washed with ether and then dried to obtain 3.74 g of mucin powder. The powder was dissolved in a saline in a concentration of 1 mg/ml and the resulting solution was subjected to repression experiments.

In the anti-I neutralization test, 2 drops of a test serum and 1 drop of the mucin solution were placed in a test tube and mixed, after which the resulting mixture was allowed to stand at room temperature for 30 minutes. Next, 1 drop of 2% O type red blood cells were added, and the mixture thus obtained was incubated at 4° C. for 20 minutes and then centrifuged at 3,400 r.p.m. for 15 seconds, after which whether agglutination had been occurred or not was visually judged. Comparatively, the same experiment was carried out as a control, except that a saline was used in place of the mucin solution.

In Table 1 are shown the results of neutralization test on 16 kinds of serum anti-I's collected from various patients requiring blood transfusion. From these results, it is obvious that the mucin prepared from hog gastric mucosa neutralize certain anti-I's.

EXAMPLE 2

In Table 1 are shown the results of neutralization tests carried out in the same manner as in Example 1, except that commercially available mucin derived from hog stomach was used. The commercially available mucin showed the same neutralization pattern as that of the mucin prepared from hog stomach.

EXAMPLE 3

235 g of bovine submaxillary gland was treated in the same manner as in Example 1 to obtain 14.8 g of mucin. The mucin was dissolved in a saline in a concentration of 1 mg/ml and tested for neutralizing activity on the 16 kinds of anti-I's in the same manner as in Example 1. The results are shown in Table 1.

EXAMPLE 4

In the same manner as in Example 1, 137 g of lamb gastric mucosa was treated to obtain 2.28 g of mucin. The neutralizing activity of the mucin on the 16 kinds of anti-I's is shown in Table 1.

EXAMPLE 5

In the same manner as in Example 1, 100 g of horse gastric mucosa was treated to obtain 1.26 g of mucin. The mucin was tested for anti-I neutralizing activity in the same manner as in Example 1. The results are shown in Table 1.

EXAMPLE 6

In the same manner as in Example 1, 10.4 g of rabbit gastric mucosa was treated to obtain 100 mg mucin. The mucin was dissolved in a saline in a concentration of 1 mg/ml and tested for neutralizing activity on the 16 kinds of anti-I's in the same manner as in Example 1. The results are shown in Table 1.

From the results in these Examples 3 to 6, it has become apparent that the mucins of bovine, sheep and horse show neutralization patterns different from those of the hog mucins in Examples 1 and 2.

EXAMPLE 7

By centrifugation, 500 ml of human milk was skimmed. The pH of the skim milk obtained was adjusted to 4.6 to 4.7 with hydrochloric acid, and the casein precipitated was centrifugally removed to obtain whey. The whey was tested, as a sample, for neutralizing activity on the anti-I's in the same manner as in Example 1. The results are shown in Table 1.

EXAMPLE 8

The same procedure as in Example 7 was repeated, except that cow's milk was used in place of human milk. The cow's milk whey thus obtained was subjected to neutralization tests in the same manner as in Example 1. From the results of these experiments shown in Table 1, it is obvious that human milk and cow's milk show the same neutralization patterns.

EXAMPLE 9

To 360 ml of chicken egg white was added 360 ml of a 1:2 mixed solution of 0.5 M trichloroacetic acid and acetone, and the resulting mixture was stirred. Acetone 2.5 times volume as much as the supernatant freed from the formed precipitate by centrifugation was added to the supernatant. The precipitate thus formed was collected by centrifugation and dissolved in distilled water, and the resulting solution was dialyzed against distilled water to obtain a chicken ovomucoid solution. The ovomucoid solution was subjected to anti-I neutralization tests in the same manner as in Example 1. The results are shown in Table 1.

EXAMPLE 10

A mixture of the same amounts of the rabbit mucin solution used in Example 6 and the cow's milk used in Example 8 was prepared. This mixture was subjected to neutralization in the same manner as in Example 1. The results are shown in Table 1. From these results, it is obvious that all the kinds of anti-I's can be neutralized by mixing these two kinds of I blood group substances.

EXAMPLE 11

There was prepared a mixture of substantially the same amount (in terms of solutions) of the hog mucin used in Example 1, the mucin derived from bovine which was used in Example 3, the mucin derived from sheep which was used in Example 4, the human milk used in Example 7 and the chicken ovomucoid obtained in Example 9. This mixture was subjected to neutralization tests in the same manner as in Example 1. The results are shown in Table 1. From these results, it is obvious that all the kinds of anti-I's can be neutralized by mixing these 5 kinds of I blood group substances.

EXAMPLE 12

The pH of the mixture of hog mucin, bovine mucin, sheep mucin, human milk and chicken ovomucoid prepared in Example 11 was adjusted to 8.5, and zeolite particles (ZEOLUM ® F-9 mfd. by Toyo Soda Kogyo Co., Ltd.) were dispersed thereinto in a concentration of 0.25%. The zeolite particles were sensitised with the I blood group substances by bringing the former into contact with the latter with gentle stirring at 37° C. for 2 hours. After completion of the sensitisation, the zeolite particles were washed with a phosphate buffer solution and suspended in a phosphate buffer solution containing 0.01% of sodium azide, whereby I blood group substances-sensitized zeolite particles were prepared.

An anti-I neutralization test was carried in the following manner. Two drops of a test serum and one drop of the I blood group substances-sensitized zeolite particles suspension were placed in a test tube, mixed, and then lightly shaken at room temperature for 30 minutes. The presence of anti-I in the supernatant freed from the zeolite particles by centrifugation was judged in the same manner as in Example 1. The results are shown in Table 1. From these results, it is obvious that even when supported on a carrier such as zeolite or the like, the above-mentioned I blood group substances can neutralize the anti-I's just as in a free state.

COMPARATIVE EXAMPLE 1

By use of a commercially available anti-I sorbent derived from rabbit erythrocyte stroma, neutralization tests were carried out in the same manner as in Example 1. The results are shown in Table 1. From these results, it is obvious that when the commercially available anti-I sorbent is used, it shows the same neutralization pattern as that of the rabbit mucin of Example 6 and cannot neutralize certain anti-I's, and that these anti-I's can also be neutralized by using the anti-I sorbent of this invention.

TABLE 1

| Test serum | Control-Saline | Example 1 Hog mucin | 2 Hog mucin | 3 Bovine mucin | 4 Sheep mucin | 5 Horse mucin | 6 Rabbit mucin | 7 Human milk | 8 Cow's milk | 9 Ovomucoid | Example 10 Mixture of two | 11 Mixture of five | 11 Supported on zeolite | Comparative Example 1 Rabbit red blood cells |
|---|---|---|---|---|---|---|---|---|---|---|---|---|---|---|
| 1 | + | − | − | + | + | − | − | + | + | + | − | − | − | − |
| 2 | + | + | + | − | + | − | − | + | + | − | − | − | − | − |
| 3 | + | + | + | + | + | + | + | − | − | + | − | − | − | + |
| 4 | + | + | + | − | − | − | − | + | + | − | − | − | − | − |
| 5 | + | − | − | − | − | − | − | + | + | + | − | − | − | − |
| 6 | + | + | + | + | + | − | + | − | − | + | − | − | − | + |
| 7 | + | − | − | + | + | + | − | + | + | + | − | − | − | − |
| 8 | + | − | − | − | − | − | − | + | + | + | − | − | − | − |
| 9 | + | + | + | + | + | + | + | − | − | + | − | − | − | + |
| 10 | + | + | + | − | + | − | − | + | + | − | − | − | − | − |
| 11 | + | + | + | − | + | − | − | + | + | + | − | − | − | − |
| 12 | + | − | − | + | + | + | − | + | + | + | − | − | − | − |
| 13 | + | + | + | + | − | − | + | − | − | + | − | − | − | + |
| 14 | + | + | + | − | + | − | − | + | + | − | − | − | − | − |
| 15 | + | − | − | − | − | − | − | + | + | + | − | − | − | − |
| 16 | + | + | + | + | + | − | − | + | + | − | − | − | − | − |

Note:
+: agglutination,
−: no agglutination

What is claimed is:

1. An anti-I sorbent which comprises as a substance having I blood group activity at least two materials selected from the group consisting of mucin from a gastric mucosa derived from Suiformes, Ruminantia, Equoidea and Lagomorpha, mucin from sub-maxilliary glands derived from bovine, saccharide from human milk or cow milk, and ovomucoid from Galli.

2. A sorbent according to claim 1, wherein the mucin is derived from Suiformes, infraclass 3 Eutheria, order 26 Artiodactyla, suborder 1.

3. A sorbent according to claim 1, wherein the mucin is derived from Lagomorpha, infraclass 3 Eutheria, order 9.

4. A sorbent according to claim 1, wherein the mucin is derived from Ruminantia, infraclass 3 Eutheria, order 26 Antiodactyla, suborder 3.

5. A sorbent according to claim 1, wherein the mucin is derived from Equoidea, infraclass 3 Eutheria, order 25 Perissodactyla, suborder 1.

6. A sorbent according to claim 1, wherein the milk is human milk.

7. A sorbent according to claim 1, wherein the ovomucoid is derived from Galli, VIII-3 subclass Ornithurae, order 16, suborder 1.

8. A sorbent according to claim 1, wherein the I blood group substance having activity are in a form of solution.

9. A sorbent according to claim 1, wherein the I blood group substances are supported on an insoluble carrier.

10. A sorbent according to claim 9, wherein the insoluble carrier is polystyrene latex particles or zeolite particles.

11. A sorbent according to claim 1 which contains 0.05 to 10 mg each of the said at least two materials per ml of serum which is to be examined with said sorbent.

12. A sorbent according to claim 1 wherein Suiformes is hog.

13. A sorbent according to claim 1 wherein Ruminantia is sheep.

14. A sorbent according to claim 1 wherein Equoidea is horse.

15. A sorbent according to claim 1 wherein Lagomorpha is rabbit.

16. A sorbent according to claim 1 wherein Galli is hen.

* * * * *